(12) United States Patent
Smailagic et al.

(10) Patent No.: US 9,094,501 B2
(45) Date of Patent: Jul. 28, 2015

(54) METHODS, SYSTEMS AND COMPUTER PROGRAM PRODUCTS FOR COLLECTING EARPIECE DATA FROM A MOBILE TERMINAL

(75) Inventors: Sead Smailagic, Lund (SE); Jesper Nilsson, Lund (SE); Martin Nystrom, Horja (SE)

(73) Assignees: Sony Corporation, Tokyo (JP); Sony Mobile Communications AB, Lund (SE)

( * ) Notice: Subject to any disclaimer, the term of this patent is extended or adjusted under 35 U.S.C. 154(b) by 146 days.

(21) Appl. No.: 13/817,881

(22) PCT Filed: Aug. 10, 2011

(86) PCT No.: PCT/IB2011/001844
§ 371 (c)(1),
(2), (4) Date: Feb. 20, 2013

(87) PCT Pub. No.: WO2013/021225
PCT Pub. Date: Feb. 14, 2013

(65) Prior Publication Data
US 2013/0149969 A1    Jun. 13, 2013

(51) Int. Cl.
*H04B 17/00* (2006.01)
*H04M 1/24* (2006.01)
*H04R 1/10* (2006.01)
*A61B 5/00* (2006.01)

(52) U.S. Cl.
CPC . *H04M 1/24* (2013.01); *H04R 1/10* (2013.01); *A61B 5/6817* (2013.01); *A61B 5/6843* (2013.01); *H04R 2225/39* (2013.01); *H04R 2225/55* (2013.01)

(58) Field of Classification Search
USPC .............. 455/66.1, 67.11, 41.1, 41.2, 41.3
See application file for complete search history.

(56) References Cited

U.S. PATENT DOCUMENTS 8,494,452 B2 *  7/2013  Fok et al. ................ 455/67.11
2007/0121959 A1  5/2007  Philipp
(Continued)

FOREIGN PATENT DOCUMENTS

WO    WO 2008/119382    10/2008

OTHER PUBLICATIONS

Notification Concerning Transmittal of International Preliminary Report on Patentability, Application No. PCT/IB2011/001844, Date of Mailing: Feb. 20, 2014; 8 pages.
(Continued)

*Primary Examiner* — Nguyen Vo
(74) *Attorney, Agent, or Firm* — Myers Bigel Sibley & Sajovec, PA

(57) ABSTRACT

A system for collecting earpiece data from a mobile terminal comprising an earpiece includes an earpiece data module in the mobile terminal configured to obtain earpiece data based on usage of the earpiece. A mobile terminal memory is in the mobile terminal and is configured to store the earpiece data. A communications module is in the mobile terminal and is configured to connect the mobile terminal to a remote earpiece data collection module that is remote to the mobile terminal. The earpiece data module is further configured to determine if the earpiece data in the mobile terminal memory satisfies a threshold and to transmit the earpiece data to the remote earpiece data collection module by the communications module if the earpiece data satisfies the threshold.

18 Claims, 4 Drawing Sheets

(56) References Cited

U.S. PATENT DOCUMENTS

2008/0146890 A1     6/2008  LeBoeuf et al.
2008/0260190 A1 *  10/2008  Kidmose ..................... 381/314
2009/0150919 A1 *   6/2009  Lee et al. ..................... 725/10

OTHER PUBLICATIONS

International Search Report and Written Opinion of the International Searching Authority for PCT/IB2011/001844 mailed May 23, 2012.

* cited by examiner

METHODS, SYSTEMS AND COMPUTER PROGRAM PRODUCTS FOR COLLECTING EARPIECE DATA FROM A MOBILE TERMINAL

CROSS-REFERENCE TO RELATED APPLICATION

This application is a 35 U.S.C. §371 national stage application of PCT International Application No. PCT/IB2011/001844, filed on 10 Aug. 2011, the disclosure and content of which is incorporated by reference herein as if set forth in its entirety.

FIELD OF THE INVENTION

The present invention relates to wireless communications and related devices, and more particularly, to methods, systems and computer program products for collecting earpiece data.

BACKGROUND

Mobile communications terminals, such as cellular phones or other audio devices, typically include a speaker on the terminal housing for emitting sound to the user's ear, and may also include a wired or wireless earpiece, such as on a headset, for emitting sound to the user's ear without requiring the user to hold the terminal next to the ear. The use of the speaker on the terminal housing may be referred to as a "handset mode" of operation, and the use of a separate headset may be referred to as a "headset mode."

Headsets may take various forms, including headphones, which are speakers that are held adjacent an outer portion of the ear, and earphones or earbuds, which are positioned inside the ear canal. Various types of headsets are referred to herein as "earpieces."

The sound characteristics as heard by the user's ear may change with the position and application of force to the user's ear, which may cause varying degrees of acoustic leakage. The leak tolerance of the particular headset may be improved by acoustical and/or mechanical designs. However, such designs may require relatively powerful and large transducers with associated disadvantages in terms of size, weight, and/or power consumption for the mobile terminal. Moreover, the leakage results in a variation in frequency response such that some frequencies are affected differently than other frequencies. For example, when the acoustic leakage is relatively large, it is generally more difficult for the user to hear low frequencies. Therefore, increasing the volume of the speaker does not adequately address problems with acoustic leakage.

SUMMARY OF EMBODIMENTS OF THE INVENTION

In some embodiments, a system for collecting earpiece data from a mobile terminal comprising an earpiece includes an earpiece data module in the mobile terminal configured to obtain earpiece data based on usage of the earpiece. A mobile terminal memory is in the mobile terminal and is configured to store the earpiece data. A communications module is in the mobile terminal and is configured to connect the mobile terminal to a remote earpiece data collection module that is remote to the mobile terminal. The earpiece data module is further configured to determine if the earpiece data in the mobile terminal memory satisfies a threshold and to transmit the earpiece data to the remote earpiece data collection module by the communications module if the earpiece data satisfies the threshold.

In some embodiments, the earpiece data module is further configured to determine, responsive to the earpiece data, whether the earpiece is in use in a user's ear, and the earpiece data satisfies the threshold when the earpiece data module determines that the earpiece is in use in the user's ear. The earpiece data module may be further configured to store the earpiece data in the mobile terminal memory if the earpiece satisfies the threshold. In some embodiments, the threshold is a first threshold, and the earpiece data module is further configured to determine if the earpiece data stored in the mobile terminal satisfies a second threshold. The communications module may be configured to initiate a connection between the mobile terminal and the remote earpiece data collection module when the earpiece data stored in the mobile terminal satisfies the second threshold. The second threshold may include an amount of earpiece data.

In some embodiments, the mobile terminal further comprises a sensor on the earpiece configured to generate the earpiece data. The sensor may include an acoustic sensor, an impedance sensor, an RF sensor, an infrared (IR) sensor, a pressure sensor and/or a capacitive sensor. The sensor may be configured to detect a position of the earpiece with respect to an ear of the user. The sensor may be configured to detect an acoustic signal.

In some embodiments, the earpiece data comprises demographic data. The demographic data may include a geographic area of the mobile terminal, a user gender, and/or a user age. In some embodiments, the remote earpiece data collection module is configured to receive earpiece data from a plurality of mobile terminals, and to classify the earpiece data responsive to the demographic data.

In some embodiments, the communications module comprises a wireless transceiver.

In some embodiments, methods for collecting earpiece data from a mobile terminal including an earpiece are provided. Earpiece data may be obtained based on usage of the earpiece at the mobile terminal. It may be determined if the earpiece data at the mobile terminal satisfies a threshold. The earpiece data may be transferred to a remote earpiece data collection module that is remote to the mobile terminal if the earpiece data at the mobile terminal memory satisfies the threshold.

In some embodiments, the methods include determining, responsive to the earpiece data, whether the earpiece is in use in a user's ear. The earpiece data may satisfy the threshold when the earpiece is determined to be in use in the user's ear. In some embodiments, the earpiece data is stored in the mobile terminal if the earpiece satisfies the threshold. In some embodiments, the threshold comprises a first threshold, and the method further includes determining if the earpiece data stored in the mobile terminal satisfies a second threshold, and initiating a connection between the mobile terminal and the remote earpiece data collection module when the earpiece data stored in the mobile terminal satisfies the second threshold.

In some embodiments, earpiece data is sensed using a sensor on the earpiece configured to generate the earpiece data. The sensor may include an acoustic sensor, an impedance sensor, an RF sensor, an infrared (IR) sensor, a pressure sensor and/or a capacitive sensor.

In some embodiments, the earpiece data includes demographic data. Earpiece data may be received from a plurality of mobile terminals at the remote earpiece data collection module, and the earpiece data may be classified responsive to the demographic data.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

Figure 1:
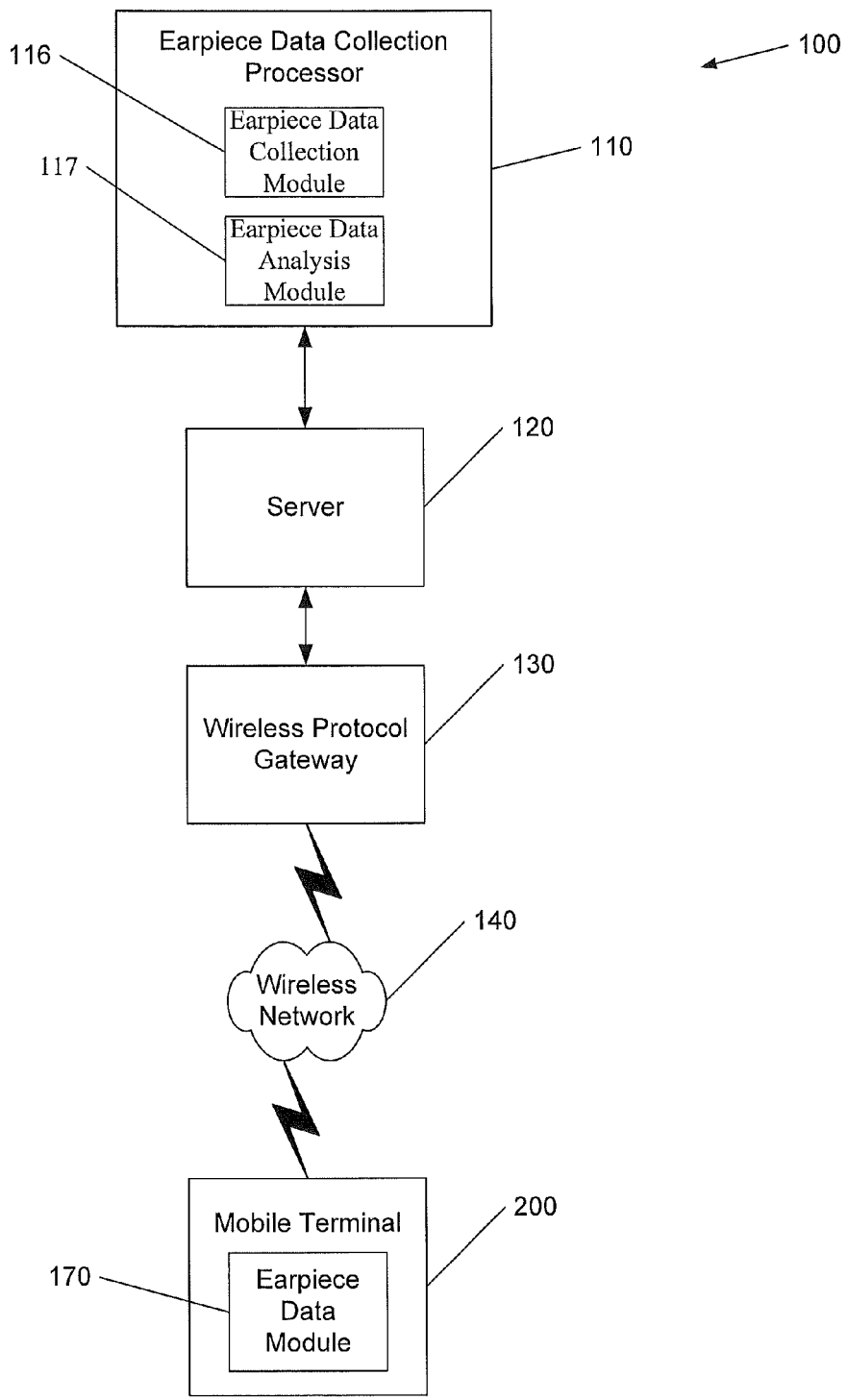
FIG. 1 is a schematic diagram of systems according to some embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

Referring now to FIG. 1, a block diagram of embodiments of the present invention implemented in a network environment will be described. The network 100 may include a mobile terminal 200, a wireless network 140, a wireless protocol gateway 130, a server 120 and an earpiece data collection processor 110. The server 120 may communicate over the wireless network 140 through the wireless protocol gateway 130. The mobile terminal 200 may also communicate over the wireless network 140. Thus, the wireless network 140 may provide a connection between the mobile terminal 200 and the server 120 through the wireless protocol gateway 130. The server 120 may be an applications server, web server or the like.

It will be understood that the present invention is not limited to the configuration illustrated in FIG. 1, and one or more elements/devices in FIG. 1 may be combined with other elements/devices and/or various functionalities described herein may be provided by different elements/devices. For example, the earpiece data collection processor 110 may be integrated with the server 120 or the earpiece data collection processor 110 may be directly connected to the wireless protocol gateway 130 or the mobile terminal 200. The wireless protocol gateway 130 may be omitted, and/or the mobile terminal 200 may communicate with the earpiece data collection processor 110 by any suitable technique, including a cellular or wireless network, a data network (e.g., the Internet and/or private data packet network) or the like. As illustrated in FIG. 1, the earpiece data collection processor 110 includes an earpiece data collection module 116 and an earpiece data analysis module 117. The earpiece data collection module 116 and/or the earpiece data analysis module 117 may be integrated with one another without departing from the teachings of the present invention. In some embodiments, the earpiece data collection processor 110 may be provided in or connected to a base station 24 (FIG. 2) and is configured to obtain and store earpiece data from the mobile terminal 200. The earpiece data collection module 116 and the earpiece data analysis module 117 may be remote to the mobile terminal 200 so that the earpiece data collection module 116 and/or earpiece data analysis module 117 may receive and/or analyze earpiece data from a plurality of mobile terminals 200. Moreover, the earpiece data of the earpiece data collection module 116 and the analysis provided by the earpiece data analysis module 117 may be accessed by the service providers and manufacturers, e.g., to improve the earpieces and acoustic devices made available to users as described herein.

Figure 2:
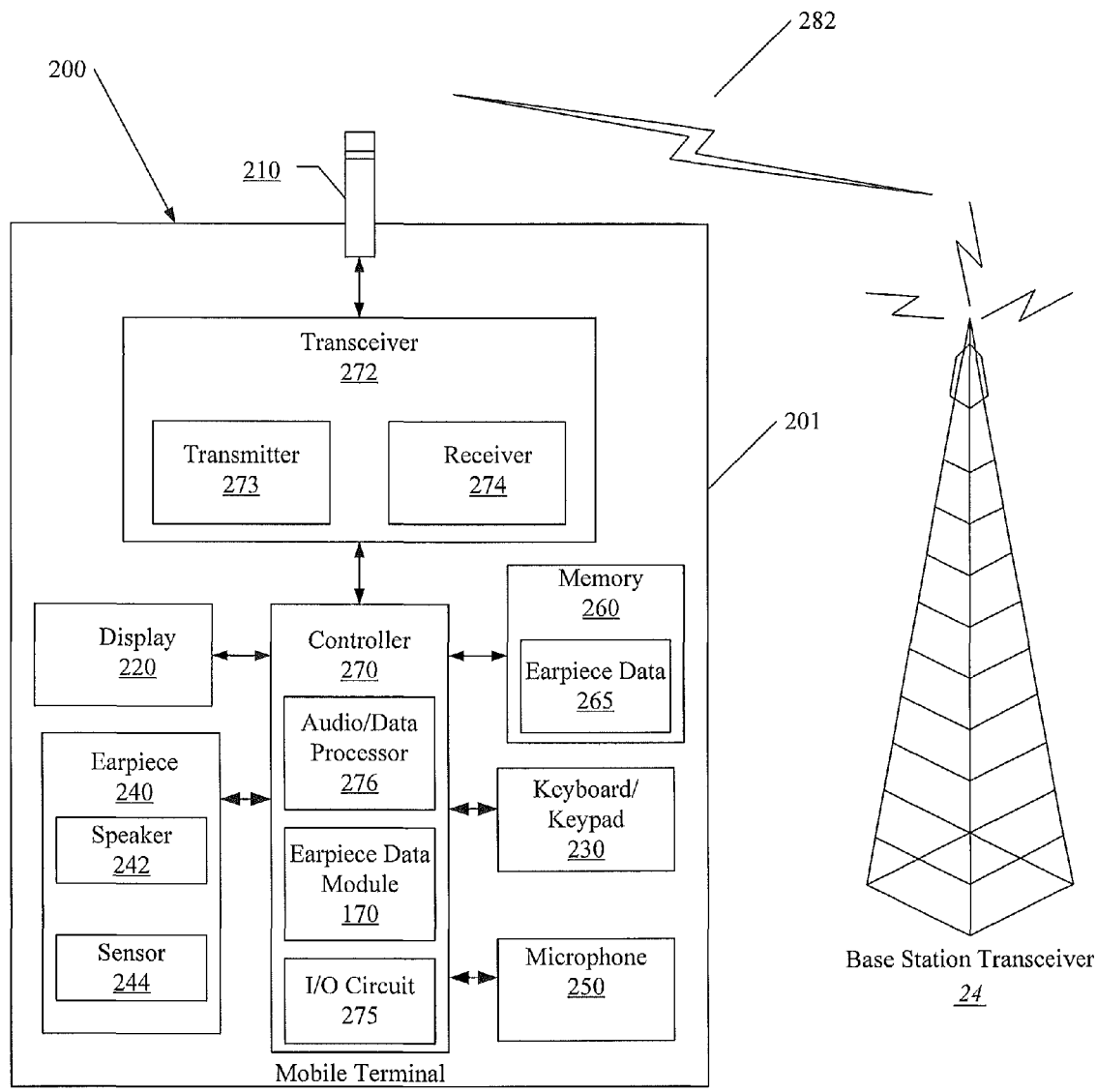
FIG. 2 is a schematic diagram of a mobile terminal and base station transceiver according to some embodiments of the present invention.

Embodiments of the present invention will now be further described with reference to the schematic block diagram illustration of a wireless terminal in FIG. 2. FIG. 2 illustrates an exemplary radiotelephone communication system, in accordance with embodiments of the present invention, that includes a mobile wireless terminal 200 and a base station transceiver 24. The mobile terminal 200 may include, in a portable housing 201, a keyboard/keypad 230, a display 220, an earpiece 240 that includes a speaker 242 and a sensor 244, a microphone 250, a transceiver 272, and a memory 260 that communicates with a controller 270.

The transceiver 272, as illustrated, includes a transmitter circuit 273 and a receiver circuit 274, which, respectively, transmits outgoing radio frequency signals to the base station transceiver 24 and receives incoming radio frequency signals from the base station transceiver 24 via an antenna 210. The radio frequency signals transmitted between the mobile terminal 200 and the base station transceiver 24 may comprise both traffic and control signals (e.g., paging signals/messages for incoming calls), which are used to establish and maintain communication with another party or destination. The transceiver 272 may further operate to provide signals from other devices in a network to/from the I/O circuit 275.

Various of the foregoing components of the mobile terminal 200, other than those described further herein, may be included in many conventional mobile terminals and their functionality is generally known to those skilled in the art. It should be further understood, that, as used herein, the term "mobile terminal" may include a cellular radiotelephone with or without a multi-line display; a Personal Communications System (PCS) terminal or "Smartphone" that may combine a cellular radiotelephone with data processing, facsimile and data communications capabilities; a Personal Data Assistant (PDA) that can include a radiotelephone, pager, Internet/ intranet access, Web browser, organizer, calendar and/or a global positioning system (GPS) receiver; and a conventional laptop and/or palmtop receiver or other appliance that includes a radiotelephone transceiver. Mobile terminals may also be referred to as "pervasive computing" devices. Mobile terminals may also include any audio device, including portable media devices.

The base station transceiver 24 includes the radio transceiver(s) that define an individual cell in a cellular network and communicate with the mobile terminal 200 and other mobile terminals in the cell using a radio-link protocol. Although only a single base station transceiver 24 is shown, it will be understood that many base station transceivers may be connected through, for example, a mobile switching center and other devices to define a wireless communication network, for example, the wireless network 140 illustrated in FIG. 1.

The controller 270 may include a audio/data processing circuit 276 as well as other functional modules and/or circuits not illustrated in FIG. 2 but which will be understood to those of skill in the art related to wireless communications, including data and voice communication support. As used herein, the audio/data processing circuit 276 may include components such as demodulators, decoders, interleavers and RF processor circuitry for processing data, including an audio signal. The controller 270, such as a microprocessor, microcontroller or similar data processing device, may execute program instructions stored in a memory 260 of the mobile terminal 200, such as a dynamic random access memory (DRAM), electrically erasable programmable read-only memory (EEPROM) or other storage device.

The transceiver 272, the audio/data processing circuit 276 and other components of the mobile terminal 200 may be implemented using a variety of hardware and software. For example, operations of the transceiver 272 and/or the audio/ data processing circuit 276 may be implemented using special-purpose hardware, such as an application specific integrated circuit (ASIC) and programmable logic devices such as gate arrays, and/or software or firmware running on a computing device such as a microprocessor, microcontroller or digital signal processor (DSP). Although functions of the transceiver 272 and the other circuits shown in FIG. 2 may be integrated in a single device, such as a single ASIC microprocessor, they may also be distributed among several devices. Aspects of these circuits may also be combined in one or more devices, such as an ASIC, DSP, microprocessor or microcontroller.

In accordance with various embodiments of the present invention, the controller 270 may include an earpiece data module 170 that is configured to collect earpiece data 265 from an earpiece 240 of the mobile terminal 200. For example, the earpiece 240 may include a sensor 244 for sensing a parameter related to the performance characteristics of the earpiece 240 and/or the earpiece speaker 242. The earpiece data 265, which is stored in memory 260, is typically collected during normal operation of the mobile terminal 200. The term "normal" as used herein may be used to describe the daily use of a mobile terminal by a user. For example, normal operation may include phone calls initiated and received, audio files accessed and played via the earpiece and the like. The earpiece data 265 collected, e.g., by the sensor 244 may include an acoustic signal, an impedance signal, RF signals, infrared (IR) signals, signals from a pressure sensor, a capacitive sensor and the like. The sensor 244 may be a single sensor in a single earpiece or may include two or more sensors in dual ear speakers. The earpiece 240 may be a headphone that is configured to be positioned outside and substantially enclose the user's ear or an in-ear earpieces such as earbuds or earphones, including canalphones, which may be configured to act as earphones and earplugs that reduce environmental noise by sealing the ear canal.

Thus, the earpiece data module 170 collects earpiece data 265 including information related to the acoustic performance of the earpiece, for example, how the acoustic performance is perceived or received by a particular user, how the earpiece fits within the ear, a degree of acoustic leakage or the like. In some embodiments, the earpiece data 265 includes an input signal to the speaker 242 and an output signal from the sensor 244. Thus, the input acoustic signal to the speaker 242 may be compared to a sensed measurement from the speaker 244, such as a sensed signal from a microphone.

In some embodiments, the sensor 244 may include more than one sensor for detecting the same or different parameters. In some embodiments, one sensor may be used for determining if the earpiece 240 is being used or is in position in the ear, and another sensor may be used to determine an acoustic quality and/or proper placement in the ear. For example, an IR sensor may detect an IR signal, which is related to a temperature adjacent the earpiece 240, to determine if the earpiece 240 is in position in the ear, and another sensor, such as an acoustic sensor or microphone, may detect an acoustic signal to determine the acoustic performance of the earpiece 240 in use (e.g., by detecting a acoustic leakage relative to the input signal to the speaker 242 such as by comparing an input signal with the detected acoustic output signal). Although an IR sensor is described in the above example, any suitable sensor may be used, such as a capacitive sensor, a pressure sensor, an impedance sensor, and the like. Such sensors may be used to detect a signal that may be interpreted to determine whether the earpiece 240 is in use in the ear and/or a degree of sound quality or proper placement of the earpiece 240. Although a microphone is described in the above example, additional sensors may be used to estimate acoustic leakage or other parameters related to earpiece performance, such as a capacitive sensor, a pressure sensor, an impedance sensor and the like. Additional parameters that may be sensed include physical data regarding the user's ear configuration, such as the length of the ear canal, the width/diameter of the ear canal, and the acoustic properties of the ear canal, including resonances and/or the damping or Q-value of the resonances. Such physical data may be measured directly or indirectly using the sensors described herein. In some embodiments, the ear speaker 242 may be a combined speaker/sensor, which receives electrical signals from the mobile terminal 200 and projects acoustic sounds and also receives incoming acoustic signals from its environment and converts the sensed acoustic signals to electric signals. Thus, the speaker 242 may provide the functionality of the sensor 244 described herein in a single unit.

In some embodiments, the same sensor may be used to collect data related to the position of the earpiece 240 and data related to the acoustic performance of the earpiece 240. For example, a transducer, an IR sensor, capacitive sensor, pressure sensor, or impedance sensor may detect parameters (e.g., IR signal, capacitance, pressure or impedance caused by the earpiece 240 touching or being in close proximity to the user's ear) that may be used to determine if the earpiece 240 is in position in the ear during the collection of additional earpiece data and/or whether the earpiece 240 is properly placed in the ear based on the degree of contact between the earpiece and the ear. For example, if the earpiece data 265 is below a threshold indicating that the earpiece 240 is likely not in use on a user (e.g., the earpiece 240 may be resting on a surface and is not positioned adjacent an ear), then any additional earpiece data 265 collected from the sensor 244 is likely not relevant and may be discarded or not stored in the earpiece data 265.

Therefore, the sensor 244 may be configured to detect various parameters for determining an acoustic quality and/or proper earpiece positioning. Sensors that may be used to detect acoustic quality and/or proper earpiece positioning include those disclosed in International Patent Application No. PCT/EP2011/002249, filed May 5, 2011; U.S. Pat. No. 6,639,987, filed Dec. 11, 2001; and U.S. Patent Publication No. 2011/0103602, filed Dec. 17, 2010, the disclosures of which are hereby incorporated by reference in their entireties. A determination regarding whether the earpiece 240 is properly placed in the ear (or a degree of proper placement) may be used for future earpiece designs. For example, the earpiece data 265 from different mobile terminals 200 may be compiled and analyzed by the earpiece data collection module 116 and the earpiece data analysis module 117 to determine, for example, if a particular earpiece design is more likely to have a higher degree of proper placement in the ear if the user is of a particular gender, ethnicity or live in a give geographic area. Thus, the data collected by the earpiece data collection module 116 may be used, for example, to tailor earpiece designs to particular markets or user demographics and to evaluate earpiece designs using a large sample size of users.

It will be understood that the earpiece data module 170 may be configured to track any one of these parameters individually or any combination thereof. Furthermore, the present invention is not intended to be limited by the above list, but is intended to include any feature or measure of performance that may provide insight into the performance of an earpiece. These examples are intended for exemplary purposes only and should not be construed as limiting the present invention.

Once the earpiece data module 170 begins to collect earpiece data 265 on the individual mobile terminals, a user may connect to the earpiece data collection processor 110 to provide the collected earpiece data 265 for analysis and use by, e.g., earpiece manufacturers and other interested entities. In some embodiments, the earpiece data 265 may be sent to a base station 24 where it may be stored and analyzed in the same way as discussed with respect to the earpiece data collection processor 110. The earpiece data collection processor 110 may include a website or other user interface for data collection and/or analysis.

As discussed above, the earpiece data collection processor 110, which may be remotely located from the mobile terminal 200, may upload and store the earpiece data 265 in the earpiece data collection module 116 of the earpiece data collection processor 110. The earpiece data collection module 116 may be configured to store multiple lists of earpiece data 265 from a plurality of mobile terminals. The data in the earpiece data collection module 116 may be analyzed to provide information that may be used to modify earpiece design and/or acoustic signals for the earpiece of the mobile terminal 200, for example, using the earpiece data analysis module 117.

In some embodiments, the earpiece data 265 may include data related to the mobile terminal 200 and/or the earpiece 240, such as the earpiece or mobile terminal model, the date that the device was purchased, the geographic area in which the device was purchased. The earpiece data 265 may also include data related to the user, such as the gender of the user, the age of the user, the height and/or weight of the user, the ethnicity of the user, the geographic area in which the user lives, and the like. Accordingly, the data analysis module 117 may correlate earpiece data 265 for a particular earpiece model and determine an acoustic performance and/or quality of fit for the earpiece 240 based on the various information, such as demographic information (geographic area, gender, age, height, weight, ethnicity, etc.) or information about the earpiece 240 (date of purchase, geographic area, model characteristics (type of materials used, mechanical characteristics, etc.)).

In some embodiments, the earpiece data module 170 of the mobile terminal 200 may be configured to periodically relay earpiece data, for example, regarding earpiece performance. For example, the earpiece data module 170 may include a quality threshold for the data, and the earpiece data module 170 may be configured to connect to the remote earpiece data collection module 116 when the quality of the earpiece data reaches the threshold. The quality threshold may be an amount of data, e.g., an amount of data that is considered sufficiently significant to send to the remote earpiece data collection module 116. In some embodiments, the quality threshold may be related to the quality of the data acquired that independent of the amount. For example, the data quality may be related to the frequencies of the audio input, and the audio input may include frequencies that are unlikely to produce quality earpiece data 265 for evaluating the earpiece 240. For earpiece data 265 that does not reach a quality threshold, for example, based on the audio input frequencies, the earpiece data module 170 may be configured to not store the earpiece data unless the audio input satisfies the quality threshold.

Figure 3:
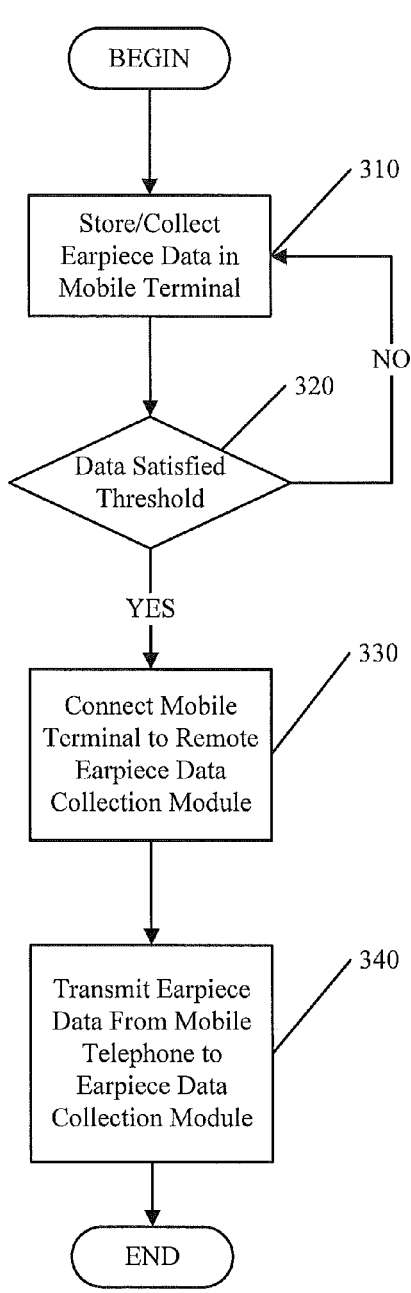
FIGS. 3-5 are flowcharts illustrating operations according to some embodiments of the present invention.

Referring to FIG. 3, operations for collecting earpiece data from a mobile terminal 200 will be discussed. The earpiece data module 170 in the mobile terminal 200 is configured to store and/or collect earpiece data 265 during operation of the mobile terminal 200 (block 310). As discussed above, the earpiece data 265 may be collected during normal operation of the mobile terminal 200 or during a designated testing cycle. The term "normal" as used herein may be used to describe the daily use of a mobile terminal by a user. For example, normal operation may include any normal use of the audio features of the mobile terminal using the earpiece including telephone usage or the use of audio (e.g., music) or audio/video file.

The earpiece module 170 determines if a data threshold, such as a quality or quantity threshold has been satisfied (block 320). If the data does not satisfy the threshold (block 320), then the data is not transmitted to a central and/or remote earpiece data collection module 116. If the data satisfies the threshold (Block 320), then the mobile terminal 200 is connected to the earpiece data collection module 116 (block 330). The mobile terminal 200 may be connected to the earpiece data collection module 116 via any suitable technique via any suitable communications connection. For example, the mobile terminal 200 may communicate with the earpiece data collection module 116 via the wireless network 140, which may include, for example, code division multiple access (CDMA), time division multiple access (TDMA), Global System for Mobile Communication (GSM), General Packet Radio Service (GPRS), Integrated Digital Enhanced Net (iDEN), Cellular Digital Packet Data (CDPD), J Phone, KDDI, Wideband Code Division Multiple Access (WCDMA) and Universal Mobile Telecommunications System (UMTS) network or the like. Communication over the network 140 may be accomplished using a wireless access protocol through the wireless protocol gateway 130. Exemplary wireless access protocols may include HyperText Transfer Protocol (HTTP), Wireless Application Protocol (WAP), SMS and Wireless Markup Language (WML) or any combination thereof, but may be any wireless protocol known to those skilled in the art. However, although embodiments according to the present invention are described with respect to the wireless protocol gateway 130 and the network 140 or base station 24, it should be understood that any suitable communications may be used, including wired and wireless communications connections and a combination thereof.

Moreover, the query regarding whether the data satisfies the threshold (Block 320) may be initiated periodically or the query may be triggered by another event, such as when the mobile terminal 200 received program updates, when the mobile terminal detects a WiFi network, when the mobile terminal 200 is connected to a charger.

When the mobile terminal 200 connects to the data collection module 116, the earpiece data 265 generated by the earpiece data module 170 and stored in the mobile terminal 200 is transmitted to the remote earpiece data collection module 116 (block 340).

Figure 4:
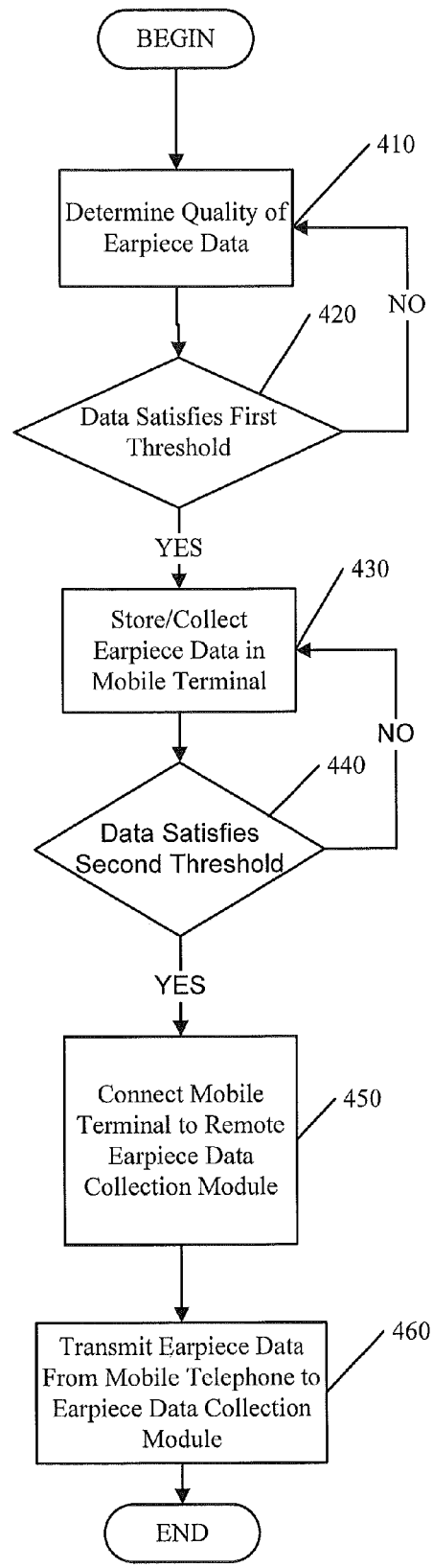

FIG. 4 is a flowchart illustrating operations according to further embodiments of the present invention. As illustrated, the earpiece data module 170 determines a quality of the earpiece data that is being collected by the mobile terminal 200 (block 410) The earpiece data module 170 may determine a quality of the data based on a measurement of whether the earpiece 240 is in the ear or the quality of the data collected or likely to be collected. Various quality determinations of the earpiece data 265 may be used at block 410 to determine if the data satisfies a first threshold (block 420) and is stored/collected in the mobile terminal (block 430).

For example, if the sensor 244 senses a degree of contact between the earpiece 240 and the ear that indicates that the earpiece 240 is not in position on the ear (e.g., based on an impedance measurement, IR measurement, pressure measurement, etc.), then the data does not satisfy the first threshold (block 420). The acoustic input signal is another example of a quality measurements. For example, the acoustic input signal to the speaker 242 may be compared with a frequency profile to determine if the acoustic input signal is likely to produce useful measurements of the performance of the earpiece 240. If the earpiece data 265 being measured includes an acoustic response signal, such as measured by an acoustic sensor or microphone, the quality of the acoustic response signal may be related to the frequency profile of the acoustic input signal. Therefore, in some embodiments, the acoustic input signal (or a frequency profile thereof) may be used to determine if the data satisfies the first threshold (block 420).

If the data satisfies a second threshold value (block 440), then the mobile terminal is connected to the remote earpiece data collection module 116 (block 450), and the earpiece data is transmitted from the mobile terminal to the earpiece data collection module 116.

Figure 5:
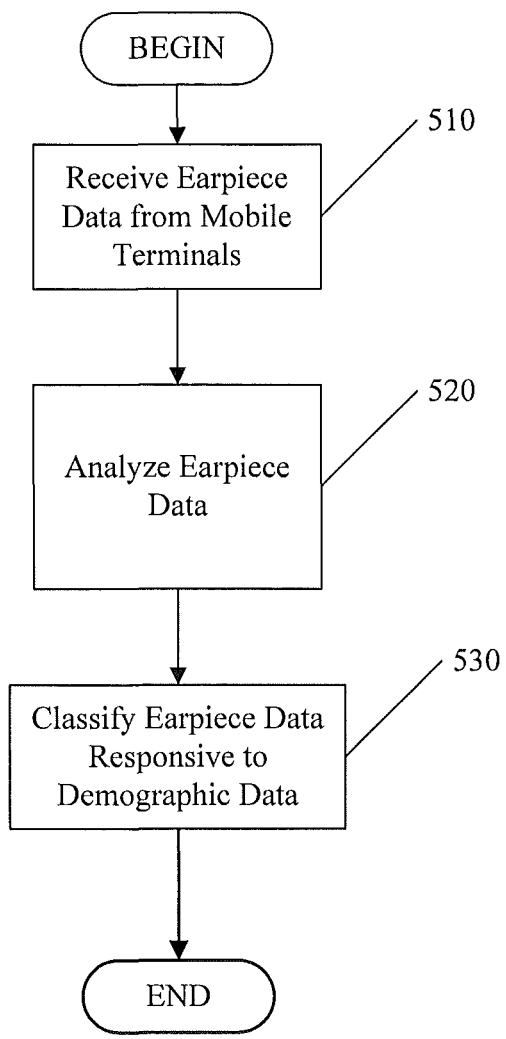

Referring to FIG. 5, the earpiece data may be received from various mobile terminals 200 (block 510). In some embodiments, data may be received by the earpiece data collection module 116 from a relatively large number of mobile terminals such as 100,000 mobile terminals, 500,000 mobile terminals, one million mobile terminals or more. Thus, the data sample size may be larger, for example, than earpiece data that is typically collected via traditional channels, such as in a laboratory or experimental setting. The earpiece data may be analyzed (block 520) by the remote earpiece data analysis module 117. In some embodiments, the earpiece data may be classified responsive to demographic data (block 530), e.g., to correlate data results with different demographics. For example, the earpiece data analysis module 117 may be used to determine if a particular model of earpiece performs better in a given geographic area or market than in another geographic area or market, and subsequent products or marketing strategies may be modified to use this information. Accordingly, earpieces may be designed, modified and/or customized for specific markets, for example, a specific geographic area, gender, age, etc. for the user as determined by the earpiece data analysis module 117. Moreover, any problems with specific earpiece models may be identified and/or corrected.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A system for collecting earpiece data from a mobile terminal comprising an earpiece, the system comprising:
    an earpiece data module in the mobile terminal configured to obtain earpiece data based on usage of the earpiece;
    a mobile terminal memory in the mobile terminal configured to store the earpiece data;
    a communications module in the mobile terminal configured to connect the mobile terminal to a remote earpiece data collection module that is remote to the mobile terminal;
    wherein the earpiece data module is further configured to determine if the earpiece data in the mobile terminal memory satisfies a transmit threshold comprising an amount of collected data and to transmit the earpiece data to the remote earpiece data collection module by the communications module if the earpiece data satisfies the transmit threshold,
    wherein the earpiece data comprises an input signal from the mobile terminal to a speaker on the earpiece and an output signal from a sensor on the earpiece such that a comparison between the input signal from the mobile terminal and the output signal of the sensor indicates an acoustic performance of the earpiece.

2. The system of claim 1, wherein the earpiece data module is further configured to determine, responsive to the earpiece data, whether the earpiece is in use in a user's ear, the earpiece data satisfying a collection threshold when the earpiece data module determines that the earpiece is in use in the user's ear, and to store the earpiece data in the mobile terminal memory if the earpiece satisfies the collection threshold.

3. The system of claim 2, wherein the communications module is configured to initiate a connection between the mobile terminal and the remote earpiece data collection module when the earpiece data stored in the mobile terminal satisfies the transmit threshold.

4. The system of claim 1, further comprising a compliance sensor comprising an impedance sensor, an RF sensor, an infrared (IR) sensor, a pressure sensor and/or a capacitive sensor.

5. The system of claim 4, wherein the compliance sensor is configured to detect a position of the earpiece with respect to an ear of the user.

6. The system of claim 1, wherein the sensor is configured to detect an acoustic signal.

7. The system of claim 1, wherein the earpiece data comprises demographic data.

8. The system of claim 7, wherein the demographic data includes a geographic area of the mobile terminal, a user gender, and/or a user age.

9. The system of claim 7, wherein the remote earpiece data collection module is configured to receive earpiece data from a plurality of mobile terminals, and to classify the earpiece data responsive to the demographic data.

10. The system of claim 1, wherein the communications module comprises a wireless transceiver.

11. The system of claim 1, wherein the input signal from the mobile terminal to a speaker on the earpiece comprises a communications signal and/or an audio file and/or an audio/video file.

12. A method for collecting earpiece data from a mobile terminal comprising an earpiece and mobile terminal memory, the method comprising:
    obtaining earpiece data based on usage of the earpiece at the mobile terminal;
    determining if the earpiece data at the mobile terminal satisfies a transmit threshold comprising an amount of collected data; and
    transmitting the earpiece data to a remote earpiece data collection module that is remote to the mobile terminal if the earpiece data at the mobile terminal memory satisfies the transmit threshold,
    wherein the earpiece data comprises an input signal from the mobile terminal to a speaker on the earpiece and an output signal from a sensor on the earpiece such that a comparison between the input signal from the mobile terminal and the output signal of the sensor indicates an acoustic performance of the earpiece.

13. The method of claim 12, further comprising determining, responsive to the earpiece data, whether the earpiece is in use in a user's ear, wherein the earpiece data satisfies a collection threshold when the earpiece is determined to be in use in the user's ear, and storing the earpiece data in the mobile terminal if the earpiece data satisfies the collection threshold.

14. The method of claim 12, initiating a connection between the mobile terminal and the remote earpiece data collection module when the earpiece data stored in the mobile terminal satisfies the transmit threshold.

15. The method of claim 12, further comprising sensing earpiece data using a sensor on the earpiece configured to generate the earpiece data.

16. The method of claim 15, wherein the sensor comprises an acoustic sensor, an impedance sensor, an RF sensor, an infrared (IR) sensor, a pressure sensor and/or a capacitive sensor.

17. The method of claim 12, wherein the earpiece data includes demographic data, the method comprising:
    receiving earpiece data from a plurality of mobile terminals at the remote earpiece data collection module; and
    classifying the earpiece data responsive to the demographic data.

18. The method of claim 12, wherein the input signal from the mobile terminal to a speaker on the earpiece comprises a communications signal and/or an audio file and/or an audio/video file.

* * * * *